United States Patent
Lee et al.

(10) Patent No.: US 11,945,772 B2
(45) Date of Patent: Apr. 2, 2024

(54) METALLOSILICATE CATALYST SOLVENTS FOR THE FORMATION OF ALKYLENE GLYCOL MONOALKYL ETHERS

(71) Applicant: Dow Global Technologies LLC, Midland, MI (US)

(72) Inventors: Wen-Sheng Lee, Midland, MI (US); Mingzhe Yu, Sugar Land, TX (US); Jing L. Houser, Midland, MI (US); Sung-Yu Ku, Manvel, TX (US); Wanglin Yu, Pearland, TX (US); Stephen W. King, Braselton, GA (US); Paulami Majumdar, Midland, MI (US); Le Wang, Pearland, TX (US)

(73) Assignee: Dow Global Technologies LLC, Midland, MI (US)

(*) Notice: Subject to any disclaimer, the term of this patent is extended or adjusted under 35 U.S.C. 154(b) by 37 days.

(21) Appl. No.: 17/627,183

(22) PCT Filed: Sep. 29, 2020

(86) PCT No.: PCT/US2020/053199
§ 371 (c)(1),
(2) Date: Jan. 14, 2022

(87) PCT Pub. No.: WO2021/067223
PCT Pub. Date: Apr. 8, 2021

(65) Prior Publication Data
US 2022/0274903 A1 Sep. 1, 2022

Related U.S. Application Data

(60) Provisional application No. 62/908,108, filed on Sep. 30, 2019.

(51) Int. Cl.
*C07C 41/06* (2006.01)

(52) U.S. Cl.
CPC .................... *C07C 41/06* (2013.01)

(58) Field of Classification Search
CPC .................................................. C07C 41/06
See application file for complete search history.

(56) References Cited

U.S. PATENT DOCUMENTS

| | | | |
|---|---|---|---|
| 5,300,126 A | 4/1994 | Brown et al. | |
| 5,741,948 A | 4/1998 | Kirishiki et al. | |
| 6,346,509 B1 | 2/2002 | Kadono et al. | |
| 6,417,408 B2 | 7/2002 | Onda et al. | |
| 8,722,944 B2 | 5/2014 | Daugs et al. | |

FOREIGN PATENT DOCUMENTS

EP 0747339 A1 12/1996

OTHER PUBLICATIONS

Yihlin Chen, "Dimethyl Phthalate (DMP) Diethyl Phthalate (DEP) Dibutyl Phthalate (DBP) DI-2-Ethylhexyl Phthalate (DEHP) DI-n-Octyl Phthalate (DNOP)", Organic Methods of Evaluation Branch, OSHA Salt Lake Technical Center, Salt Lake City Utah, Aug. 1994, pp. 1-31 (Year: 1994).*
Gaudin, "Acid-Catalyzed Etherification of Glycerol with Long-Alkyl-Chain-Alcohols", ChemSusChem, 2011, 4, pp. 719-722.
Klepacova, "Etherification of Glycerol and Ethylene Glycol by Isobutylene", Applied Catalysis A: General, 2007, 328, pp. 1-13.
Liu, "Hydrophobic Solid Acids and Their Catalytic Applications in Green and Sustainable Chemistry", ACS Catal., 2018, 8, pp. 372-391.
Parvulescu, "Chemical Imaging of Catalyst Deactivation during the Conversion of Renewables at the Single Particle Level: Etherification of Biomass-Based Polyols with Alkenes over H-Beta Zeolites", J. Am. Chem. Soc., 2010, 132, pp. 10429-10439.
Parvulescu, "Synthesis of Octyl-Ethers of Biomass-Based Glycols Through Two Competitive Catalytic Routes: Telomerization and Etherification", Catal. Today, 2010, 158, pp. 130-138.
Ruppert, "Synthesis of Long Alkyl Chain Ethers Through Direct Etherification of Biomass-Based Alcohols with 1-Octene Over Heterogeneous Acid Catalysts", J. Catal., 2009, 268, pp. 251-259.
Yang, "A Biodiesel Additive: Etherification of 5-Hydroxymethylfurfural with Isobutene to Tert-Butoxymethylfurfural", Catal. Sci. Technol., 2015, 5, pp. 4602-4612.
Zapata, "Hydrophobic Zeolites for Biofuel Upgrading Reactions at the Liquid-Liquid Interface in Water/Oil Emulsions", J. Am. Chem. Soc., 2012, 134, pp. 8570-8578.

* cited by examiner

*Primary Examiner* — Rosalynd A Keys
(74) *Attorney, Agent, or Firm* — Arthur R. Rogers

(57) ABSTRACT

A method including the step contacting an olefin, an alcohol, a metallosilicate catalyst and a solvent, wherein the solvent comprises structure (I): wherein $R_1$ and $R_2$ are each selected from the group consisting of an aryl group and an alkyl group with the proviso that at least one of $R_1$ and $R_2$ is an aryl group, further wherein n is 1-3.

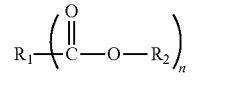

12 Claims, No Drawings

METALLOSILICATE CATALYST SOLVENTS FOR THE FORMATION OF ALKYLENE GLYCOL MONOALKYL ETHERS

BACKGROUND

Field of the Invention

The present disclosure generally relates to metallosilicate catalysts and more specifically to solvents used in conjunction with metallosilicate catalysts.

Introduction

Production of secondary alcohol ethoxylate surfactants can be carried out by the catalyzed ethoxylation of (poly)alkylene glycol monoalkyl ether ("monoalkyl ether"). The monoalkyl ether is formed from an olefin and a (poly)alkylene glycol using metallosilicate catalysts. Metallosilicate catalysts offer a selectivity for monoalkyl ether of greater than 80% which is advantageous as (poly)alkylene glycol dialkyl ether ("dialkyl ether") is deleterious to properties of the secondary alcohol ethoxylate surfactants.

Although providing selectivity for monoalkyl ether as high as 85%, the metallosilicate catalysts foul quickly resulting in short in-service times, low monoalkyl ether production rates and the need for repeated catalyst regeneration steps. The use of solvents has been disclosed in connection with the formation of monoalkyl ether, but solvents were believed to have no or little effect on the reaction. For example, U.S. Pat. No. 5,741,948 ("'948 patent") explains that "the reaction between olefin and (poly)alkylene glycol can be conducted in the presence or absence of a solvent" and that the solvent can be "nitromethane, nitroethane, nitrobenzene, dioxane, ethylene glycol dimethyl ether, sulfolane, benzene, toluene, xylene, hexane, cyclohexane, decane, paraffin, etc." As apparent from the optional nature and wide variety of solvents provided in the '948 patent, the presence or type of solvent was not believed to affect the monoalkyl ether reaction.

Accordingly, it would be surprising and unexpected to discover a solvent that when used with metallosilicate catalysts increases monoalkyl ether selectivity to greater than 85% while maintaining monoalkyl ether production rates.

SUMMARY

The present invention offers a solution to providing a solvent that when used with metallosilicate catalysts increases monoalkyl ether selectivity to greater than 85% while maintaining monoalkyl ether production rates.

The present invention is a result of discovering that solvents comprising aryl groups and ester groups ("aromatic ester solvents") provide both an increase in monoalkyl ether selectivity as well as increased monoalkyl ether production rates. Such a result is surprising in that despite the conventional ambivalence toward the use of solvents in olefin and alcohol reactions, the addition of aromatic ester solvents is able to provide monoalkyl ether selectivity increases of greater than 10% while providing sustained monoalkyl ether production rates longer than conventional solvents. Further, the use of aromatic ester solvents demonstrates greater monoalkyl ether production rates and greater than 90% monoalkyl ether selectivity than conventionally utilized solvents.

According to a first feature of the present invention, a method includes the step contacting an olefin, an alcohol, a metallosilicate catalyst and a solvent, wherein the solvent comprises structure (I):

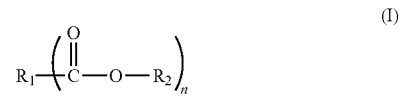

wherein $R_1$ and $R_2$ are each selected from the group consisting of an aryl group and an alkyl group with the proviso that at least one of $R_1$ and $R_2$ is an aryl group, further wherein n is 1-3.

According to a second feature of the present disclosure, the alcohol is monoethylene glycol or diethylene glycol, glycerol or combinations thereof.

According to a third feature of the present disclosure, the method may also include a step of generating an alkylene glycol monoalkyl ether.

According to a fourth feature of the present disclosure, the olefin comprises a $C_{12}$-$C_{14}$ alpha-olefin.

According to a fifth feature of the present disclosure, the metallosilicate catalyst has a silica to alumina ratio from 10 to 300.

According to a sixth feature of the present disclosure, the solvent is from 50 wt % to 80 wt % of the combined olefin, alcohol, and a solvent.

According to a seventh feature of the present disclosure, $R_1$ is an aryl group and $R_2$ is an alkyl group.

According to an eighth feature of the present disclosure, $R_1$ is selected from the group consisting of phenyl and naphthyl, $R_2$ is a linear or branched alkyl having the formula $(CH_2)_m CH_3$ wherein m is from 0-10.

According to a ninth feature of the present disclosure, the solvent is selected from the group consisting of dimethyl phthalate, diethyl phthalate, dibutyl phthalate, methyl benzoate, ethyl benzoate, trimethyl 1, 2, 4-benzentricarboxylate and combinations thereof.

According to a tenth feature of the present disclosure, the step of contacting the olefin, the alcohol, the metallosilicate catalyst and the solvent, further comprises: the contacting the olefin, the alcohol, the metallosilicate catalyst, the solvent and a second solvent comprising an ether group.

According to an eleventh feature of the present disclosure, the second solvent is selected from the group consisting of dimethoxyethane, bis(2-methoxyethyl) ether and combinations thereof.

According to a twelfth feature of the present disclosure, an alcohol to olefin molar ratio is from 2.0 to 15.

DETAILED DESCRIPTION

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

All ranges include endpoints unless otherwise stated.

Test methods refer to the most recent test method as of the priority date of this document unless a date is indicated with the test method number as a hyphenated two-digit number. References to test methods contain both a reference to the testing society and the test method number. Test method organizations are referenced by one of the following abbreviations: ASTM refers to ASTM International (formerly known as American Society for Testing and Materials); EN refers to European Norm; DIN refers to Deutsches Institut für Normung; and ISO refers to International Organization for Standards.

IUPAC codes describing Crystal structures as delineated by the Structure Commission of the International Zeolite Association refer to the most recent designation as of the priority date of this document unless otherwise indicated.

As used herein, the term weight percent ("wt %") designates the percentage by weight a component is of a total weight of an indicated composition.

Method

The method of the present invention is directed to the use of solvents in a metallosilicate catalyzed reaction of alcohol and olefin. The method may comprise steps of (a) contacting an olefin, an alcohol, a metallosilicate catalyst and a solvent and (b) generating an alkylene glycol monoalkyl ether.

Olefin

The olefin used in the method may be linear, branched, acyclic, cyclic, or mixtures thereof. The olefin may have from 5 carbons to 30 carbons (i.e., C5-C30). The olefin may have 5 carbons or greater, or 6 carbons or greater, or 7 carbons or greater, or 8 carbons or greater, or 9 carbons or greater, or 10 carbons or greater, or 11 carbons or greater, or 12 carbons or greater, or 13 carbons or greater, or 14 carbons or greater, or 15 carbons or greater, or 16 carbons or greater, or 17 carbons or greater, or 18 carbons or greater, or 19 carbons or greater, or 20 carbons or greater, or 21 carbons or greater, or 22 carbons or greater, or 23 carbons or greater, or 24 carbons or greater, or 25 carbons or greater, or 26 carbons or greater, or 27 carbons or greater, or 28 carbons or greater, or 29 carbons or greater, while at the same time, 30 carbons or less, or 29 carbons or less, or 28 carbons or less, or 27 carbons or less, or 26 carbons or less, or 25 carbons or less, or 24 carbons or less, or 23 carbons or less, or 22 carbons or less, or 21 carbons or less, or 20 carbons or less, or 19 carbons or less, or 18 carbons or less, or 17 carbons or less, or 16 carbons or less, or 15 carbons or less, or 14 carbons or less, or 13 carbons or less, or 12 carbons or less, or 11 carbons or less, or 10 carbons or less, or 9 carbons or less, or 8 carbons or less, or 7 carbons or less, or 6 carbons or less.

The olefin may include alkenes such as alpha ($\alpha$) olefins, internal disubstituted olefins, or cyclic structures (e.g., $C_3$-$C_{12}$ cycloalkene). $\alpha$ olefins include an unsaturated bond in the $\alpha$-position of the olefin. Suitable a olefins may be selected from the group consisting of propylene, 1-butene, 1-hexene, 4-methyl-1-pentene, 1-heptene, 1-octene, 1-decene, 1-dodecene, 1-tetradecene, 1-hexadecene, 1-octadecene, 1-icosene, 1-docosene and combinations thereof. Internal disubstituted olefins include an unsaturated bond not in a terminal location on the olefin. Internal olefins may be selected from the group consisting of 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene and combinations thereof. Other exemplary olefins may include butadiene and styrene.

Examples of suitable commercially available olefins include NEODENE™ 6-XHP, NEODENE™ 8, NEODENE™ 10, NEODENE™ 12, NEODENE™ 14, NEODENE™ 16, NEODENE™ 1214, NEODENE™ 1416, NEODENE™ 16148 from Shell, The Hague, Netherlands.

Alcohol

The alcohol utilized in the method may comprise a single hydroxyl group, may comprise two hydroxyl groups (i.e., a glycol) or may comprise three hydroxyl groups. The alcohol may include 1 carbon or greater, or 2 carbons or greater, or 3 carbons or greater, or 4 carbons or greater, or 5 carbons or greater, or 6 carbons or greater, or 7 carbons or greater, or 8 carbons or greater, or 9 carbons or greater, while at the same time, 10 carbons or less, or 9 carbons or less, or 8 carbons or less, or 7 carbons or less, or 6 carbons or less, or 5 carbons or less, or 4 carbons or less, or 3 carbons or less, or 2 carbons or less. The alcohol may be selected from the group consisting of methanol, ethanol, monoethylene glycol, diethylene glycol, propylene glycol, triethylene glycol, polyethylene glycol, monopropylene glycol, dipropylene glycol, tripropylene glycol, polypropylene glycol, 1,3-propanediol, 1,2-butanediol, 2,3-butanediol, 1,4-butanediol, 1,6-hexanediol, 1,4-cyclohexanemethanediol, glycerol and/or combinations thereof. According to various examples, the alcohol is a (poly)alkylene glycol such as monoethylene glycol, diethylene glycol, propylene glycol and triethylene glycol.

A molar ratio of alcohol to olefin in the method may be from be 20:1 or less, or 15:1 or less, or 10:1 or less, or 9:1 or less, or 8:1 or less, or 7:1 or less, or 6:1 or less, or 5:1 or less, or 4:1 or less, or 3:1 or less, or 2:1 or less, or 0.2:1 or less, while at the same time, 0.1:1 or greater, or 1:1 or greater, or 1:2 or greater, or 1:3 or greater, or 1:4 or greater, or 1:5 or greater, or 1:6 or greater, or 1:7 or greater, or 1:8 or greater, or 1:9 or greater, or 1:10 or greater, or 1:15 or greater, or 1:20 or greater. In specific examples, the molar ratio of the alcohol to the olefin may be from 2.0 to 15 or from 2.0 to 8. Molar ratio is calculated by dividing the number of moles of alcohol present by the number of moles of olefin present.

Solvent

One or more solvents are contacted with the olefin, the alcohol and the metallosilicate catalyst in order to facilitate a chemical reaction. The solvent has structure (I)

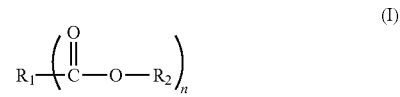

(I)

wherein $R_1$ and $R_2$ are each selected from the group consisting of an aryl group and an alkyl group with the proviso that at least one of $R_1$ and $R_2$ comprises an aryl group. As highlighted above, the inclusion of an aryl group and an ester group renders the solvent an aromatic ester solvent. Structure (I) has an n value of 1-3.

As used herein, the terms "aryl" and "aryl group" refer to an organic radical derived from aromatic hydrocarbon by deleting one hydrogen atom therefrom. An aryl group may be a monocyclic and/or fused ring system, each ring of which suitably contains from 5 to 7, or from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. As such, $R_1$ may be selected form the group consisting of phenyl and naphthyl. Aryl and aryl groups also include substituted aryls. As used herein, a "substituted aryl" refers to an aryl in which one or more hydrogen atom bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio, nitro, and both saturated and unsaturated cyclic hydrocarbons which are fused to the aromatic ring(s), linked covalently or linked to a common group such as a methylene or ethylene moiety. The common linking group may also be a carbonyl as in benzophenone or oxygen as in diphenylether or nitrogen in diphenylamine.

As used herein, the terms "alkyl" and "alkyl group" refer to a saturated linear, cyclic, or branched hydrocarbon group. Alkyls and alkyl groups also include substituted alkyls. "Substituted alkyl," refers to an alkyl in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. According to various examples, the alkyl may be a linear or branched alkyl having the formula $(CH_2)_m CH_3$ wherein m is from 0-10.

The solvent may be selected from the group consisting of dimethyl phthalate, diethyl phthalate, dibutyl phthalate, methyl benzoate, ethyl benzoate, 1,2,4-benzenetricarboxylate and combinations thereof. The solvent may be from 0.1 wt % to 85 wt % of the combined olefin, alcohol and solvent weight. The solvent may be 0.1 wt % or greater, or 0.5 wt % or greater, or 1 wt % or greater, or 5 wt % or greater, or 10 wt % or greater, or 15 wt % or greater, or 20 wt % or greater, or 25 wt % or greater, or 30 wt % or greater, or 35 wt % or greater, or 40 wt % or greater, or 45 wt % or greater, or 50 wt % or greater, or 55 wt % or greater, or 60 wt % or greater, or 65 wt % or greater, or 70 wt % or greater, or 75 wt % or greater, or 80 wt % or greater, while at the same time, 85 wt % or less, or 80 wt % or less, or 75 wt % or less, or 70 wt % or less, 65 wt % or less, or 60 wt % or less, 55 wt % or less, or 50 wt % or less, 45 wt % or less, or 40 wt % or less, 35 wt % or less, or 30 wt % or less, 25 wt % or less, or 20 wt % or less, 15 wt % or less, or 10 wt % or less, 5 wt % or less, or 1 wt % or less, or 0.5 wt % or less.

A second solvent may be combined or contacted with the olefin, alcohol, solvent and metallosilicate catalyst. The second solvent may comprise one or more ether groups. An ether group comprises an oxygen atom connected to two alkyl or aryl groups. The ether group of the second solvent may be symmetric or not symmetric. The second solvent comprising the ether group may be selected from the group consisting of dimethoxyethane, bis(2-methoxyethyl) ether, triethylene glycol dimethyl ether, dichlorobenzene, dimethyl acetamide and combinations thereof. As such, the step of contacting the olefin, the alcohol, the metallosilicate catalyst and the solvent may further comprise contacting the olefin, the alcohol, the metallosilicate catalyst, the solvent and a second solvent comprising an ether group.

A weight ratio of the solvent to the second solvent used may be 100:1 or less, or 90:1 or less, or 80:1 or less, or 70:1 or less, or 60:1 or less, or 50:1 or less, or 40:1 or less, or 30:1 or less, or 20:1 or less, or 10:1 or less, or 5:1 or less, or 2:1 or less, or 1:1 or less, while at the same time, 1:1 or greater, or 1:2 or greater, or 1:5 or greater, or 1:10 or greater, or 1:20 or greater, or 1:30 or greater, or 1:40 or greater, or 1:50 or greater, or 1:60 or greater, or 1:70 or greater, or 1:80 or greater, or 1:90 or greater, or 1:100 or greater.

Metallosilicate Catalyst

As used herein the term "metallosilicate catalyst" is an aluminosilicate (commonly referred to as a zeolite) compound having a crystal lattice that has had one or more metal elements substituted in the crystal lattice for a silicon atom. The crystal lattice of the metallosilicate catalyst form cavities and channels inside where cations, water and/or small molecules may reside. The substitute metal element may include one or more metals selected from the group consisting of B, Al, Ga, In, Ge, Sn, P, As, Sb, Sc, Y, La, Ti, Zr, V, Cr, Mn, Pb, Pd, Pt, Au, Fe, Co, Ni, Cu, Zn. The metallosilicate catalyst may be substantially free of Hf. According to various examples, the metallosilicate may have a silica to alumina ratio of from 5:1 to 1,500:1 as measured using Neutron Activation Analysis. The silica to alumina ratio may be from 5:1 to 1,500:1, or from 10:1 to 500:1, or from 10:1 to 400:1, or from 10:1 to 300:1 or from 10:1 to 200:1. Such a silica to alumina ratio may be advantageous in providing a metallosilicate catalyst with an appropriate hydrophobic selectivity that adsorb non-polar organic molecules.

The metallosilicate catalyst may have one or more ion-exchangeable cations outside the crystal lattice. The ion-exchangeable cation may include $H^+$, $Li^+$, $Na^+$, $Rb^+$, $Cs^+$, $Mg^{2+}$, $Ca^{2+}$, $Sr^{2+}$, $Ba^{2+}$, $Sc^{3+}$, $Y^{3+}$, $La^{3+}$, $R_4N^+$, $R_4P^+$ (where R is H or alkyl).

The metallosilicate catalyst may take a variety of crystal structures. Specific examples of the metallosilicate catalyst structures include MFI (e.g. ZSM-5), MEL (e.g. ZSM-11), BEA (e.g. β-type zeolite), FAU (e.g. Y-type zeolite), MOR (e.g. Mordenite), MTW (e.g. ZSM-12), and LTL (e.g. Linde L), as described using IUPAC codes in accordance with nomenclature by the Structure Commission of the International Zeolite Association.

The crystalline frameworks of metallosilicate catalyst are represented by networks of molecular-sized channels and cages comprised of corner-shared tetrahedral $[TO_4]$ (T=Si or Al) primary building blocks. A negative charge can be introduced onto the framework via the isomorphous substitution of a framework tetravalent silicon by a trivalent metal (e.g., aluminum) atom. The overall charge neutrality is then achieved by the introduction of cationic species compensating for the resulting negative lattice charge. When such a charge-compensation is provided by protons, Brønsted acid sites are formed rendering the resulting H-forms of zeolites strong solid Brønsted acids.

The metallosilicate catalysts may be used in the method in a variety of forms. For example, the metallosilicate catalysts may be powdered (e.g., particles having a longest linear dimension of less than 100 micrometers), granular (e.g., particles having a longest linear dimension of 100 micrometers or greater), or molded articles (e.g., pellets or extrudates) of powdered and/or granular metallosilicate catalysts.

The metallosilicate catalysts may have a surface area of 100 $m^2/g$ or greater, or 200 $m^2/g$ or greater, or 300 $m^2/g$ or greater, or 400 $m^2/g$ or greater, or 500 $m^2/g$ or greater, or 600 $m^2/g$ or greater, or 700 $m^2/g$ or greater, or 800 $m^2/g$ or greater, or 900 $m^2/g$ or greater, while at the same time, 1000 $m^2/g$ or less, or 900 $m^2/g$ or less, or 800 $m^2/g$ or less, or 700 $m^2/g$ or less, or 600 $m^2/g$ or less, or 500 $m^2/g$ or less, or 400 $m^2/g$ or less, or 300 $m^2/g$ or less, or 200 $m^2/g$ or less. Surface area is measured according to ASTM D4365-19.

Metallosilicate catalysts can be synthesized by hydrothermal synthesis methods. For example, the metallosilicate catalysts can be synthesized from heating a composition comprising a silica source (e.g., silica sol, silica gel, and alkoxysilanes), a metal source (e.g., metal sulfates, metal oxides, metal halides, etc.), and a quaternary ammonium salt such as a tetraethylammonium salt or tetrapropylammonium to a temperature of about 100° C. to about 175° C. until a crystal solid forms. The resulting crystal solid is then filtered off, washed with water, and dried, and then calcined at a temperature form 350° C. to 600° C.

Examples of suitable commercially available, metallosilicate catalysts include CP814E, CP814C, CP811C-300, CBV 712, CBV 720, CBV 760, CBV 2314, CBV 10A from ZEOLYST INTERNATIONAL™ of Conshohocken, PA.

Generating Monoalkyl Ether

Contacting the olefin, alcohol, metallosilicate catalyst and solvent in the generation of an alkylene glycol monoalkyl ether. The chemical reaction between the olefin and the alcohol is catalyzed by the metallosilicate catalyst in a reactor to generate the monoalkyl ether. Various monoalkyl ethers may be produced for different applications by varying which olefin is utilized and/or by varying which alcohol is utilized. Monoalkyl ether are utilized for a number of applications such as solvents, surfactants, and chemical intermediates, for instance.

The reaction of the olefin and the alcohol may take place at from 50° C. to 300° C. or from 100° C. to 200° C. In a specific example the reaction may be carried out at 150° C. Reaction of the olefin and the alcohol may be carried out in a batch reactor, continuous reactor or fixed-bed reactor. In operation of the chemical reaction, the Brønsted acid sites of the metallosilicate catalyst catalyze the etherification of the olefin to the alcohol through an addition type reaction. The reaction of the olefin and the alcohol produces the monoalkyl ether.

The addition reaction of the olefin to the glycol may form not only monoalkyl ether but also the dialkyl ether. The metallosilicate catalyst may exhibit a selectivity to produce alkylene monoalkyl ether, but not dialkyl ether. The monoalkyl ether selectivity may be 70% or greater, or 75% or greater, or 80% or greater, or 85% or greater, or 90% or greater, or 95% or greater or 99% or greater, while at the same time, 100% or less, or 95% or less, or 90% or less, or 85% or less, or 80% or less, or 75% or less. The dialkyl ether selectivity may be 0% or greater, or 2% or greater, or 4% or greater, or 6% or greater, or 8% or greater, or 10% or greater, or 12% or greater, or 14% or greater, or 16% or greater, or 18% or greater, while at the same time, 20% or less, or 18% or less, or 16% or less, or 14% or less, or 12% or less, or 10% or less, or 8% or less, or 6% or less, or 4% or less, or 2% or less.

A monoalkyl ether yield is calculated by multiplying the amount of olefin conversion by the monoalkyl ether selectivity. The alkylene glycol monoalkyl ether yield may be 10% or greater, or 15% or greater, or 20% or greater, or 25% or greater, or 30% or greater, or 35% or greater, while at the same time, 40% or less, or 35% or less, or 30% or less, or 25% or less, or 20% or less, or 15% or less. Monoalkyl ether yield is a measure of the catalytic activity and selectivity and is a good measure of the production rate of the metallosilicate catalyst.

During the reaction of the olefin and the alcohol, the catalyst becomes fouled and results it the deactivating (i.e., lost etherification activity >90%) the catalyst within hours.

EXAMPLES

Materials

Catalyst is a metallosilicate catalysts defined by a BEA structure and having a silica to alumina ratio of 25:1 and a surface area of 680 $m^2/g$, that is commercially available as CP814E from ZEOLYST INTERNATIONAL™ of Conshohocken, PA.

1-Dodecene is an alpha olefin that is commercially available as NEODENE™ 12 from the SHELL™ group of The Hague, Netherlands.

Monoethylene Glycol is liquid anhydrous ethylene glycol purchased from SIGMA ALDRICH™ having a CAS Number of 107-21-1.

DME is a Dimethoxyethane that is a liquid anhydrous solvent purchased from SIGMA ALDRICH™ having a CAS Number of 110-71-4.

Diglyme is bis(2-methoxyethyl) ether that is a liquid anhydrous solvent purchased from SIGMA ALDRICH™ having a CAS Number of 111-96-6.

Hexane is a liquid solvent purchased from FISHER CHEMICAL™ having a CAS number of 110-54-3.

Methyl trimethylacetate is a liquid solvent purchased from SIGMA ALDRICH™ having a CAS Number of 598-98-1.

Methyl propionate is a liquid solvent purchased from SIGMA ALDRICH™ having a CAS Number of 554-12-1.

Methyl benzoate is a liquid solvent purchased from SIGMA ALDRICH™ having a CAS Number of 93-58-3

Ethyl benzoate is a liquid solvent purchased from SIGMA ALDRICH™ having a CAS Number of 93-89-0.

Diethyl phthalate is a liquid solvent purchased from SIGMA ALDRICH™ having a CAS Number of 84-66-2.

Dimethyl phthalate is a liquid solvent purchased from SIGMA ALDRICH™ having a CAS Number of 131-11-3.

Diethyl phthalate is a liquid solvent purchased from SIGMA ALDRICH™ having a CAS Number of 84-66-2.

Dibutyl phthalate is a liquid solvent purchased from SIGMA ALDRICH™ having a CAS Number of 84-74-2.

1,2,4-benzenetricarboxylate is Trimethyl 1,2,4-benzenetricarboxylate purchased from SIGMA ALDRICH™ having a CAS Number of 2459-10-1.

Triglyme is triethylene glycol dimethyl ether commercially available from SIGMA ALDRICH™ having a CAS Number of 112-49-2.

Test Methods

Gas Chromatography Samples

Prepare gas chromatography samples by mixing 100 μL of the example with 10 mL of gas chromatography solution that was prepared by addition of 1 mL of hexadecane in 1 L of ethyl acetate. Analyze the sample using an Agilent 7890B gas chromatography instrument. Determine the total amount of 1-dodecene derived species, which includes monoalkyl ether, dialkyl ether and 2-dodecanol, total amount of dodecene, which includes 1-dodecene and all non 1-dodecene other $C_{12}$ isomers. Table 1 provides the relevant gas chromatography instrument parameters.

TABLE 1

| Chromatograph: | Agilent 7890 Series GC |
|---|---|
| Column: | Agilent HP88, 100 m × 0.25 mm × 0.20 um |
| Detector | FID |
| Oven: | 50° C.-7 min-6° C./min-260° C.-1 min |
| Injector: | 250° C. |
| Detector: | 300° C. |
| Carrier: | Helium 2.0 mL/min constant flow mode |
| Split ratio: | 10 |
| Make-Up: | Nitrogen 25 mL/min |
| Air: | 400 mL/min |
| Hydrogen: | 40 mL/min |
| Inlet Liner: | Restek PN 23305.5 Sky Precision Liner with wool |
| Sample Size: | 1 μL |
| GC vial rinsing solvent: | ethyl acetate |

Time-On-Stream (TOS)

Calculate the TOS of the catalyst by measuring the total time the catalyst has been in contact with the monoethylene glycol, dodecene, catalyst, solvent and products at temperatures above 60° C.

Olefin Conversion

Calculate the percent olefin conversion by dividing the total amount of dodecene derived species by the summation of total amount of dodecene derived species and the amount of dodecene. Multiply the quotient by 100.

Monoalkyl Ether Selectivity

Calculate the percent monoalkyl ether selectivity by dividing the total amount of monoalkyl ether by the total amount of dodecene derived species. Multiply the quotient by 100.

Monoether Yield

Calculate the monoalkyl ether yield by multiplying the olefin conversion value by the monoalkyl ether selectivity value.

Catalyst Activity

Calculate the catalyst activity by dividing the grams of monoalkyl ether produced by the grams of catalyst used and dividing the quotient by the hours of the reaction.

Sample Preparation

Detailed below is the preparation of inventive examples 1-15 ("IE1-IE15") and comparative examples 1-12 ("CE1-CE12").

Inventive Example 1

Prepare IE1 by attaching a heating jacket and controller to a 300 mL Parr reactor having a pitch blade impeller for agitation. Load a single-phase mixture of 24.9 grams (g) monoethylene glycol, 16.9 g of 1-dodecene and 88.2 g DME solvent to the reactor together with 2.04 g of catalyst in powdered form. Seal the reactor. Heat the reactor to 135° C. under 850 rpm agitation. Heat for 0.5 hours at 135° C. Remove the heating jacket and allow the reactor to passively cool down to 60° C. in 0.25 hour. Take a sample from a reactor port and prepared for gas chromatography (GC) analysis. Immediately reattach the heating jacket to the reactor. Heat the reactor for 0.5 hours at 135° C. Remove the heating jacket and allow the reactor to passively cool down to 60° C. in 0.25 hour. Take a sample from a reactor port and prepared for gas chromatography (GC) analysis. Immediately reattach the heating jacket to the reactor. Repeat the process at time intervals of 0.75 hours with effective heating times of 135° C. of 0.5 hour. Disregard samples with less than 1.5 hours of time on stream due to startup effects.

Comparative Example 1

Prepare CE1 in the identical manner as IE1, except do not include DME solvent.

Inventive Example 2

Prepare IE2 by attaching a heating jacket and controller to a 300 mL Parr reactor having a pitch blade impeller for agitation. Load a total of 20.3 g of catalyst in 1.58 mm pellet form into a catalyst basket. Place the catalyst basket in the reactor along with 20.46 g of 1-dodecene, 30.25 g of monoethylene glycol ("MEG"), and 99.3 g diglyme. Heat the reactor to 135° C. and hold for 4 hours. Remove the heating jacket and allow the reactor to cool to ambient conditions. Collect liquids in the reactor as a single phase and prepare the liquid for GC analysis. Recharge the reactor with 20.46 g of 1-dodecene, 30.25 g of monoethylene glycol, and 99.3 g diglyme with the catalyst basket not changed. Repeat heating, holding, removing the liquid and recharging for another four times to accumulate a total time on stream of 20 hours for the catalyst in the catalyst basket.

Comparative Example 2

Prepare CE2 in an identical manner as IE2, except do not include diglyme solvent and adjust 1-dodecene and monoethylene glycol volumes. Replace the lost diglyme solvent volume by using 81.9 g of 1-dodecene and 121 g of monoethylene glycol. Repeat heating and sampling identical to IE2.

Inventive Example 3

Prepare IE3 by attaching a heating jacket and controller to a 300 mL Parr reactor having a pitch blade impeller for agitation. Load a total of 20.3 g of catalyst in 1.58 mm pellet form into a catalyst basket. Place the catalyst basket in the reactor along with 20.46 g of 1-dodecene, 30.25 g of monoethylene glycol, and 99.3 g dimethyl phthalate. Heat the reactor to 135° C. and hold for 4 hours. Remove the heating jacket and allow the reactor to cool to ambient conditions. Collect liquids in the reactor as a single phase and prepare the liquid for GC analysis. Recharge the reactor with 20.46 g of 1-dodecene, 30.25 g of monoethylene glycol, and 99.3 g dimethyl phthalate with the catalyst basket nuchanged. Repeat heating, holding, removing the liquid and recharging for another four times to accumulate a total time on stream of 20 hours for the catalyst in the catalyst basket.

Inventive Examples 4-9 and Comparative Examples 3-10

Prepare IE4-IE11 and CE3-CE10 by attaching a heating jacket and controller to a 300 mL Parr reactor having a pitch blade impeller for agitation. Load the indicated amount of catalyst in powder form into the reactor together with 20 g of 1-dodecene, 20 g of monoethylene glycol, and either 100 g of the indicated solvent or no solvent. For CE3 and CE6, 70 g of 1-dodecene and 70 g of monoethylene glycol were used. For CE4 and CE7, 62 g of 1-dodecene and 67 g of monoethylene glycol were used. For IE10, 50 grams of each solvent indicated were used. Heat the reactor to the indicated temperature and hold for the indicated time. Remove the heating jacket and allow the reactor to cool to ambient conditions. Collect the liquid for GC analysis.

Inventive Examples 12-15 and Comparative Examples 11 and 12

Prepare IE12-IE15, CE11 and CE12 by attaching a heating jacket and controller to a 300 mL Parr reactor having a pitch blade impeller for agitation. Loaded 7.5 g of catalyst in powder form into the reactor together with indicated amounts of monoethylene glycol, 1-dodecene and solvent(s). Heated the reactor to 135° C. and liquid samples were collected at different times on stream. Once desired time on stream was reached, removed the heating jacket and allowed the reactor to cool to ambient conditions. Collected liquids in the reactor as a single phase and prepared the liquid for GC analysis. The reactor was then heated back to 135° C. for the next sampling at desired time on stream. The time required for heating and cooling was not counted as the reaction time and only the duration at 135° C. was considered for effective TOS. The data shown in Table 4 with indicated reaction time reflected the maximum olefin conversion that could be achieved during the time on stream. For CE11, 2.5 grams of fresh catalyst in powder form was added to the reactor (with total 10 g of catalyst in the reactor) after the liquid sample at 7 hours time on stream was taken and the reaction was proceeded for another 4 hours to reach 11 hours time on stream and the liquid sample was collected.

Results

Table 2 provides the percent olefin conversion, the monoalkyl ether ("ME") selectivity and catalyst activity for CE1 and CE2 that do not include a solvent and IE1-IE3 that all include solvents.

Table 2 demonstrates that the use of solvents comprising an ether group (i.e., IE1 and IE2) and solvents comprising an aryl and an ester group (i.e., IE3) can significantly decrease the rate of catalyst deactivation and improve the catalyst long-term performance. For example, over the measured time on stream IE1 has a retained catalyst activity 90% greater than CE1 and IE2 has a retained catalyst activity 70% greater than CE2. IE3 includes the aromatic ester dimethyl phthalate. As can be seen by Table 2, IE3 exhibits increased catalyst activity with time while having higher monoalkly production rates (i.e., as indicated by the olefin conversion) than CE2 and IE2 while maintaining comparable monoalkyl ether selectivity values.

Table 3 demonstrates the affect no solvent and different solvents have on monoalykl ether selectivity, olefin conversion and ME yield.

TABLE 3

| Sample | Reaction Time (h) | Temp. (° C.) | Catalyst Loading (g) | Solvent | Olefin Conversion (%) | ME Selectivity (%) | ME Yield (%) |
|---|---|---|---|---|---|---|---|
| CE3 | 2 | 135 | 5.0 | none | 16 | 85 | 13 |
| CE4 | 1 | 135 | 7.5 | none | 26 | 79 | 21 |
| CE5 | 2 | 135 | 5.0 | hexane | 12 | 85 | 10 |
| CE6 | 3 | 125 | 5.0 | none | 11 | 84 | 9 |
| CE7 | 3 | 125 | 7.5 | none | 24 | 69 | 17 |
| CE8 | 3 | 125 | 5.0 | hexane | 10 | 83 | 8 |
| CE9 | 3 | 125 | 5.0 | methyl trimethylacetate | 10 | 85 | 8 |
| CE10 | 3 | 125 | 5.0 | methyl propionate | 12 | 83 | 10 |
| IE4 | 2 | 135 | 5.0 | diglyme | 23 | 92 | 21 |
| IE5 | 2 | 135 | 5.0 | ethyl benzoate | 31 | 87 | 27 |
| IE6 | 2 | 135 | 5.0 | diethyl phthalate | 33 | 86 | 28 |
| IE7 | 3 | 125 | 5.0 | dimethyl phthalate | 26 | 85 | 22 |
| IE8 | 3 | 125 | 5.0 | diethyl phthalate | 25 | 95 | 24 |
| IE9 | 3 | 125 | 5.0 | dibutyl phthalate | 16 | 87 | 14 |
| IE10 | 2 | 135 | 5.0 | diethyl phthalate and diglyme | 24 | 84 | 20.1 |
| IE11 | 2 | | 5.0 | trimethyl 1,2,4-benzenetricarboxylate | 57 | 80 | 45.6 |

TABLE 2

| Sample | Solvent | TOS (h) | Olefin Conversion (%) | ME selectivity (%) | Catalyst activity (g ME/h/gcat) |
|---|---|---|---|---|---|
| CE1 | No Solvent | 1.50 | 25.56 | 84.17 | 1.55 |
| | | 2.25 | 31.04 | 82.53 | 0.93 |
| | | 3.00 | 33.75 | 81.57 | 0.43 |
| | | 3.75 | 36.19 | 80.40 | 0.35 |
| | | 4.50 | 37.71 | 80.02 | 0.24 |
| IE1 | DME | 1.50 | 15.01 | 91.54 | 0.88 |
| | | 2.25 | 18.51 | 92.85 | 0.78 |
| | | 3.00 | 20.64 | 93.64 | 0.49 |
| | | 3.75 | 23.65 | 91.46 | 0.52 |
| | | 4.50 | 25.72 | 92.04 | 0.46 |
| CE2 | No Solvent | 4 | 9.22 | 98.62 | 0.13 |
| | | 8 | 7.57 | 99.18 | 0.10 |
| | | 12 | 6.92 | 100.00 | 0.10 |
| | | 16 | 6.03 | 100.00 | 0.08 |
| | | 20 | 5.64 | 100.00 | 0.08 |
| IE2 | Diglyme | 4 | 42.26 | 86.73 | 0.13 |
| | | 8 | 44.66 | 89.23 | 0.14 |
| | | 12 | 44.87 | 90.22 | 0.14 |
| | | 16 | 44.92 | 90.47 | 0.14 |
| | | 20 | 43.63 | 89.45 | 0.13 |
| IE3 | Dimethyl Phthalate | 4 | 55.13 | 91.89 | 0.18 |
| | | 8 | 58.69 | 91.12 | 0.18 |
| | | 12 | 66.91 | 90.92 | 0.21 |
| | | 16 | 69.41 | 91.37 | 0.22 |
| | | 20 | 68.24 | 91.46 | 0.22 |

As can be seen from the data of Table 3, the addition of solvents comprising an ether group and solvents comprising both aromatic groups and ester groups can increase the monoalkyl ether yield as well as the monoalkyl ether selectivity as compared to no solvent or other solvents.

The ether group comprising diglyme solvent of IE4 demonstrates improved catalyst activity in the form of higher olefin conversion and monoalkyl ether yields while maintaining ME selectivity higher than 85% under similar reaction conditions as compared to CE3-CE10 which include reactions having no solvent, alkane solvents (i.e., hexane) and ester solvents that are non-aromatic (i.e., methyl trimethylacetate and methyl propionate).

IE5-IE9 all utilize aromatic ester solvents comprising both an aryl group and an ester group. Samples utilizing solvents comprising both an aryl group and an ester group produce monoalkyl ether yields that are increased by as much as 200% relative to samples CE3-CE10 including no solvent or a non-ether, non-aromatic ester solvents. Further, samples IE5-IE9 demonstrate comparable or greater monoalkyl ether selectivity than CE3-CE10 that have no solvent or a non-ether and non-aromatic ester solvent.

CE9 and CE10 demonstrate that use of solvents having an ester group but no aryl group, such as methyl trimethylacetate and methyl propionate, do not improve or degrade catalyst activity relative to none solvent samples such as CE6.

TABLE 4

| Sample | Reactant amount (g) | Reaction time (h) | Wt % Dodecene | Wt % MEG | Solvent Type | Solvent (wt %) | MEG/Olefin molar ratio | Olefin conversion (%) | ME selectivity (%) |
|---|---|---|---|---|---|---|---|---|---|
| CE11 | 150 | 11 | 30 | 10 | Triglyme | 60 | 0.8 | 30 | 60.7 |
| CE12 | 150 | 7 | 15 | 5 | Diglyme | 80 | 1 | 18.5 | 82.1 |
| IE12 | 183 | 6 | 20 | 20 | Triglyme | 60 | 2.7 | 51.2 | 85.2 |
| IE13 | 120 | 5 | 14 | 14 | Diglyme | 72 | 2.7 | 39.5 | 86.9 |
| IE14 | 160 | 4 | 9.4 | 24.6 | Diglyme/methyl benzoate | 66 | 7.1 | 50.2 | 94.2 |
| IE15 | 100 | 3 | 10 | 30 | Triglyme | 60 | 8.1 | 53.4 | 93.2 |

CE11 and CE12 demonstrate that when the monoethylene glycol/olefin ratio is below 2.5 one or both of the olefin conversion and monoether selectivity are below acceptable levels (i.e., 30% olefin conversion or greater and 80% monoether selectivity or greater). Contrarily, IE12-IE15 demonstrate that when the monoethylene glycol/olefin ratio is 2.5 or greater both the olefin conversion and monoether selectivity achieve acceptable levels. In Table 4, the solvent of IE14 is 57.6 diglyme and 8.2% methyl benzoate.

What is claimed is:

1. A method, comprising the step:
  contacting an olefin, an alcohol, a metallosilicate catalyst and a solvent, wherein the solvent comprises structure (I):

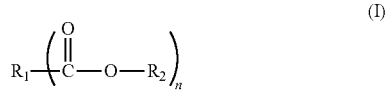

(I)

wherein $R_1$ and $R_2$ are each selected from the group consisting of an aryl group and an alkyl group with the proviso that at least one of $R_1$ and $R_2$ is an aryl group, further wherein n is 1-3.

2. The method of claim 1, wherein the alcohol is monoethylene glycol or diethylene glycol, glycerol or combinations thereof.

3. The method of claim 1, further comprising the step of: generating an alkylene glycol monoalkyl ether.

4. The method of claim 1, wherein the olefin comprises a $C_{12}$-$C_{14}$ alpha-olefin.

5. The method of claim 1, wherein the metallosilicate catalyst has a silica to alumina ratio from 10 to 300.

6. The method of claim 5, wherein the solvent is from 50 wt % to 80 wt % of the combined olefin, alcohol, and a solvent.

7. The method of claim 1, wherein $R_1$ is an aryl group and $R_2$ is an alkyl group.

8. The method of claim 7, wherein $R_1$ is selected from the group consisting of phenyl and naphthyl, $R_2$ is a linear or branched alkyl having the formula $(CH_2)_m CH_3$ wherein m is from 0-10.

9. The method of claim 8, wherein the solvent is selected from the group consisting of dimethyl phthalate, diethyl phthalate, dibutyl phthalate, methyl benzoate, ethyl benzoate, trimethyl 1, 2, 4-benzentricarboxylate and combinations thereof.

10. The method of claim 1, wherein the step of contacting the olefin, the alcohol, the metallosilicate catalyst and the solvent, further comprises:
  contacting the olefin, the alcohol, the metallosilicate catalyst, the solvent and a second solvent comprising an ether group.

11. The method of claim 10, wherein the second solvent is selected from the group consisting of dimethoxyethane, bis(2-methoxyethyl) ether, triethylene glycol dimethyl ether and combinations thereof.

12. The method of claim 1, wherein an alcohol to olefin molar ratio is from 2.0 to 15.

* * * * *